United States Patent
Sullivan

(10) Patent No.: US 12,232,879 B2
(45) Date of Patent: Feb. 25, 2025

(54) ATRIAL FIBRILLATION DETECTION

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 775 days.

(21) Appl. No.: 17/390,780

(22) Filed: Jul. 30, 2021

(65) Prior Publication Data

US 2022/0409118 A1  Dec. 29, 2022

Related U.S. Application Data

(60) Provisional application No. 63/216,187, filed on Jun. 29, 2021.

(51) Int. Cl.
*A61B 5/361* (2021.01)
*A61B 5/00* (2006.01)
*A61B 5/33* (2021.01)

(52) U.S. Cl.
CPC ............... *A61B 5/361* (2021.01); *A61B 5/33* (2021.01); *A61B 5/7217* (2013.01)

(58) Field of Classification Search
CPC ..... A61B 2505/07; A61B 5/256; A61B 5/282; A61B 5/33; A61B 5/352; A61B 5/353; A61B 5/361; A61B 5/4848; A61B 5/6823; A61B 5/6831; A61B 5/7203; A61B 5/7217; A61B 5/7221
See application file for complete search history.

(56) References Cited

U.S. PATENT DOCUMENTS 3,724,355 A  4/1973  Busch et al.
3,724,455 A  4/1973  Unger
(Continued)

FOREIGN PATENT DOCUMENTS

DE  102005060985 A1  6/2007
EP  2305110 A1  4/2011
(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — George Manuel
(74) *Attorney, Agent, or Firm* — Polsinelli PC

(57) ABSTRACT

Embodiments of a wearable monitoring device system can include one or more dry ECG electrodes and a processor that can be configured with one or more algorithms for detecting atrial fibrillation (AF) from sensed ECG signals sensed by the one or more dry ECG electrodes, and optionally other signals. In some embodiments the algorithms include one or more AF detection algorithms and optionally a noise detection algorithm. In some embodiments the wearable monitoring device or a remote system that receives data from the wearable medical device may calculate and/or characterize AF burden from ECG signals sensed by the one or more dry ECG electrodes.

20 Claims, 9 Drawing Sheets

COMPONENTS OF
SAMPLE WCD SYSTEM

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2009/0171227 A1* | 7/2009 | Dziubinski ............ A61B 5/363 600/516 |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0114167 A1* | 4/2014 | Reaser, Jr. ............ A61B 5/339 600/393 |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |

(56) References Cited

U.S. PATENT DOCUMENTS

| | | |
|---|---|---|
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| EP | 3380189 B1 | 10/2018 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012064604 A1 | 5/2012 |
| WO | 2012/151160 A1 | 11/2012 |
| WO | 2015/056262 A1 | 4/2015 |

OTHER PUBLICATIONS

Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.
Pagan-Carlo, et al., "Encircling Overlapping Multipulse Shock Waveforms for Transthoracic Defibrillation," JACC Journals, Dec. 1998, vol. 32 Issue 7, p. 2065-2071.
Zoll, LifeVest, Proven protection from Sudden Cardiac Death, 2017, 4 pages. Pittsburgh PA, USA.
International Search Report and Written Opinion for PCT Application No. PCT/US2015/051726, dated May 20, 2016, European Patent Office, Rijswijk, 11 pages.

* cited by examiner

COMPONENTS OF SAMPLE WCD SYSTEM

*MULTIPLE ELECTRODES FOR SENSING ECG SIGNALS ALONG DIFFERENT VECTORS*

*SAMPLE COMPONENTS OF A WCD SYSTEM WITH AF DETECTION*

700

| ANALYSIS | CLASSIFICATION | |
|---|---|---|
| All channels AF | AF | 710 / 720 |
| All channels No AF | No AF | 730 |
| All channels Noise | Noise | 740 |
| Some channels AF, some noise | AF | 750 |
| Some channels No AF, some noise | No AF | |
| Some channels AF, some No AF, some Noise | Vote based on the number of channels reporting AF vs No AF. If the number of channels is equal, assume No AF. | 760 |

| PATIENT REPORT: John Doe, January 1, 20XX | | |
|---|---|---|
| CLASSIFICATION | PERCENTAGE | |
| NO AF DETECTED | 10% | 820 |
| AF DETECTED | 50% | 830 |
| AF SUSPECTED | 25% | 840 |
| NOISE | 15% | 850 |

FIG. 8

ATRIAL FIBRILLATION DETECTION

CROSS REFERENCE TO RELATED PATENT APPLICATIONS

This patent application claims benefit of U.S. Provisional Patent Application No. 63/216,187 filed Jun. 29, 2021, and is incorporated herein by reference in their entirety for all purposes.

BACKGROUND

When people suffer from some types of heart arrhythmias, the result may be that blood flow to various parts of the body is reduced. Some arrythmias are of a type called atrial fibrillation (AF). While not directly life threatening, untreated AF can increase the risk of strokes, so some physicians monitor a patient for AF and calculate AF burden (related to the amount of time a patient is in AF) to help make treatment decisions for AF patients. Some other arrhythmias may even result in a Sudden Cardiac Arrest (SCA). SCA can lead to death very quickly, e.g. within 10 minutes, unless treated in the interim.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and thus save the patient's life.

All subject matter discussed in this Background section of this document is not necessarily prior art and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present disclosure describes instances and examples of cardiac monitoring systems (e.g., WCD systems), devices, systems, storage media that may store programs, and methods. This summary is provided to introduce a selection of concepts in a simplified form that are further described below. This summary is not intended to identify key features of the claimed subject matter, nor is it intended to be used as an aid in determining the scope of the claimed subject matter.

In embodiments, a wearable monitoring device can include one or more dry ECG electrodes and a processor. In some embodiments, the wearable monitoring device can be configured with one or more algorithms for detecting atrial fibrillation (AF) from sensed ECG signals sensed by the one or more dry ECG electrodes, and optionally other signals. In some embodiments, a remote system that can receive data from the wearable medical device can be configured with one or more algorithms for detecting AF. In some embodiments, the one or more AF detection algorithms can include a noise detection algorithm and/or be used with one or more separate noise detection algorithms. In some embodiments the wearable monitoring device or a remote system that receives data from the wearable medical device may calculate and/or characterize AF burden from ECG signals sensed by the one or more dry ECG electrodes. The foregoing summary is illustrative only and not intended in any way to be limiting.

BRIEF DESCRIPTION OF THE DRAWINGS

FIG. 7 is a diagram illustrating a table summarizing an AF classification algorithm, according to embodiments.

FIG. 8 is a diagram illustrating a table summarizing AF burden characterization, according to embodiments.

DETAILED DESCRIPTION

A wearable medical device system according to embodiments may protect an ambulatory patient by monitoring a patient's ECG and, in some embodiments, electrically restarting the patient's heart. Such a system may have a number of components. These components can be provided separately as modules that can be interconnected, or can be combined with other components, and so on.

Figure 1:
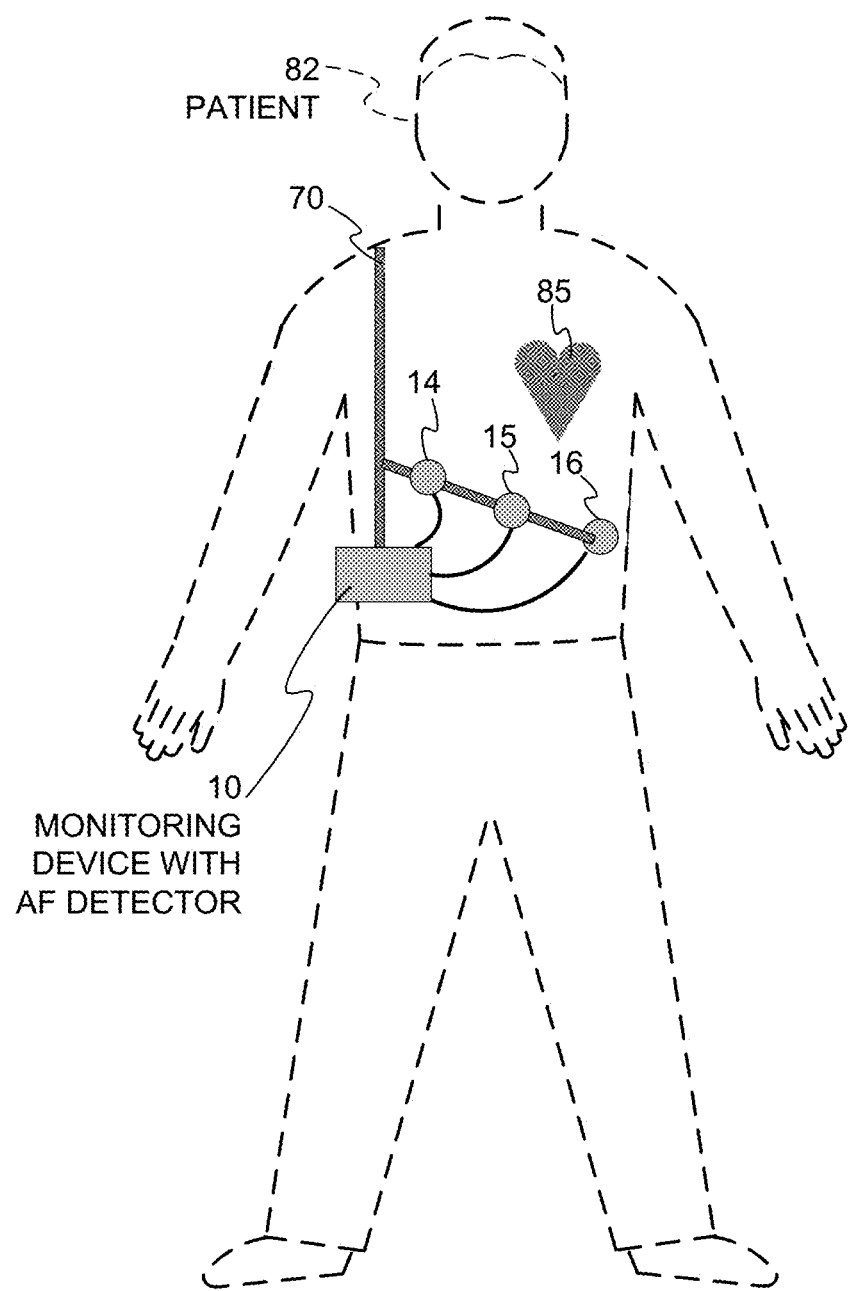
FIG. 1 is a diagram of components of a sample wearable medical device system, according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the wearable medical device (WMD) system, patient 82 can walk around and is not necessarily bed-ridden. While patient 82 may be considered to be also a "user" of the WMD system, this is not a requirement. For instance, a user of the WMD may also be a clinician such as a doctor, nurse, emergency medical technician (EMT) or other similarly tasked individual or group of individuals. In some cases, a user may even be a bystander. The particular context of these and other related terms within this description should be interpreted accordingly.

In particular, FIG. 1 also depicts components of a WMD system made according to embodiments. One such component is a support structure 70 that is wearable by ambulatory patient 82. Accordingly, support structure 70 is configured to be worn by ambulatory patient 82 for at least several hours per day, and for at least several days, even a few months. It will be understood that support structure 70 is shown only generically in FIG. 1, and in fact partly conceptually. FIG. 1 is provided merely to illustrate concepts about support structure 70, and is not to be construed as limiting how support structure 70 is implemented, or how it is worn.

Support structure 70 can be implemented in many different ways. For example, it can be implemented in a single component or a combination of multiple components. In embodiments, support structure 70 could include a vest, a half-vest, a garment, etc. In such embodiments such items can be worn similarly to analogous articles of clothing. In embodiments, support structure 70 could include a harness, one or more belts or straps, etc. In such embodiments, such items can be worn by the patient around the torso, hips, over the shoulder, etc. In embodiments, support structure 70 can include a container or housing, which can even be waterproof. In such embodiments, the support structure can be worn by being attached to the patient's body by adhesive material, for example as shown and described in U.S. Pat. No. 8,024,037. Support structure 70 can even be implemented as described for the support structure of US Pat. App. No. US2017/0056682, which is incorporated herein by reference. In light of the present disclosure, a person skilled in the art will recognize that additional components of the WMD system can be in the housing of a support structure instead of being attached externally to the support structure, for example as described in the US2017/0056682 document. There can be other examples.

FIG. 1 shows a sample monitoring device 10 configured with an AF detector. Monitoring device 10 can be connected to ECG electrodes 14, 15, and 16 coupled to support structure 70 as shown in FIG. 1, while in other embodiments more than three ECG are used to implement two or more ECG channels (sometime also referred to as vectors) as will be described in more detail below. In some embodiments, one or more ECG electrodes can be disposed in or on monitoring device 10 to be used with ECG electrodes coupled to support structure 70 to implement the multiple channels. In still other embodiments, three or more ECG electrodes are disposed in or on monitoring device 10 to implement multiple ECG channels.

In embodiments, ECG electrodes 14-16 can be configured to monitor patient 82 in a number of ways. For instance, monitoring device 10 and ECG electrodes 14-16 can be coupled to support structure 70, directly or indirectly. In other words, support structure 70 can be configured to be worn by ambulatory patient 82 so as to maintain at least one of ECG electrodes 14-16 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of monitoring device 10 can be considered coupled to support structure 70 directly, or indirectly via at least one of ECG electrodes 14-16.

When ECG electrodes 14-16 make good electrical contact with the body of patient 82, monitoring device 10 can monitor multiple channels of electrical activity of the patient's heart 85. Embodiments of multichannel ECG monitoring are described below in conjunction with FIGS. 4 and 5.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

In embodiments, one or more of the components of the shown WCD system may be customized for patient 82. This customization may include a number of aspects. For instance, support structure 70 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WMD system, in order to make its diagnoses more accurate, since patients' bodies differ from one another. Of course, such parameter values can be stored in a memory of the WMD system, and so on. Moreover, a programming interface can be made according to embodiments, which receives such measured values of baseline physiological parameters. Such a programming interface may input automatically in the WMD system these, along with other data.

Figure 2:
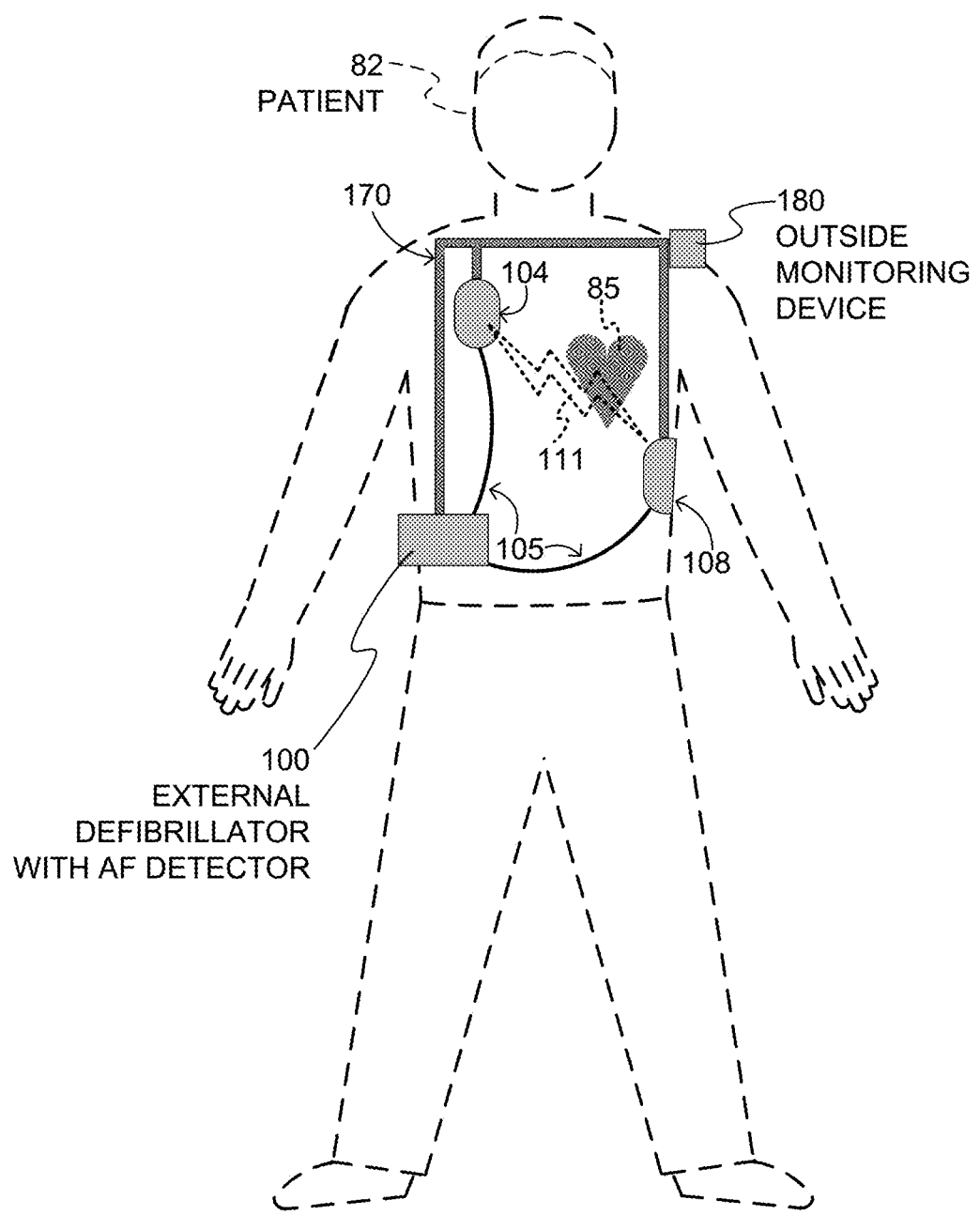
FIG. 2 is a diagram of components when the wearable medical device system of FIG. 1 is implemented using a sample WCD system, according to embodiments.

FIG. 2 depicts components of a WCD system, which in embodiments includes an AF detector (not shown) described below in conjunction with FIGS. 6-8. The WCD system is similar to the WMD system of FIG. 1, except that the wearable medical device is implemented using a WCD. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 2, and in fact partly conceptually. FIG. 2 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat.

No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 2 shows a sample external defibrillator 100 which in embodiments includes an AF detector (not shown) described below in conjunction with FIGS. 6-8. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 2 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as patient physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 3:
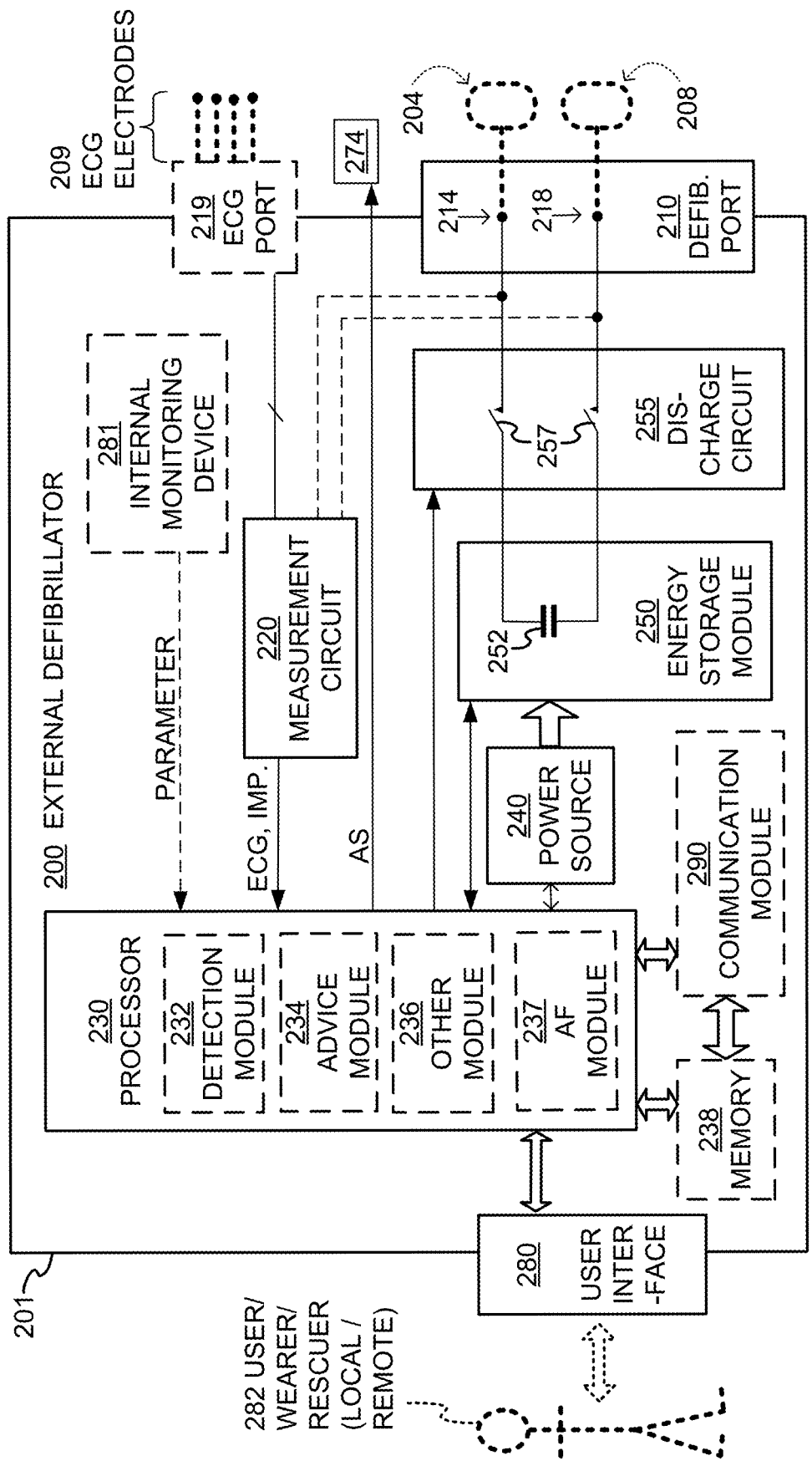
FIG. 3 is a diagram showing sample components of an external defibrillator, such as the one used in the WCD system of FIG. 2, according to embodiments.

FIG. 3 is a diagram showing components of an external defibrillator 200, made according to embodiments. These components can be, for example, included in external defibrillator 100 of FIG. 2. The components shown in FIG. 3 can be provided in a housing 201, which may also be referred to as casing 201.

External defibrillator 200 is intended for a patient who would be wearing it, such as ambulatory patient 82 of FIG. 2. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 2. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 2, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 3. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018, and since published as US 2019/0030351 A1, and also in U.S. patent application Ser. No. 16/038,007, filed on Jul. 17, 2018, and since published as US 2019/0030352 A1, both incorporated herein by reference.

Processor 230 can include additional modules, such as other module 236, for other functions. In addition, if internal monitoring device 281 is indeed provided, processor 230 may receive its inputs, etc.

In accordance with embodiments of the present disclosure, processor 230 includes an AF module 237. For example, AF module 237 can be used in implementing the AF detector of external defibrillator 100 (FIG. 2). Likewise for WMD 10 (FIG. 1), an AF module substantially similar to AF module 237 can be in the AF detector of WMD 10. Embodiments of AF module 237 are configured to analyze multichannel ECG signals to detect AF and/or suspected AF and, optionally, determine AF Burden and/or other metric or metrics related to AF burden, as described below in conjunction with FIGS. 6-8.

In other embodiments, external defibrillator 200 can include a separate processing unit (not shown) to analyze multichannel ECG signals to detect AF and/or suspected AF and, optionally, determine AF Burden and/or other metric or metrics related to AF burden, as described below in conjunction with FIGS. 6-8.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282 if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. Published Patent App. Pub. No. 20140043149A1 entitled "MOBILE COMMUNICATION DEVICE & APP FOR WEARABLE DEFIBRILLATOR SYSTEM". This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open. Defibrillator 200 can optionally include other components.

Figure 4:
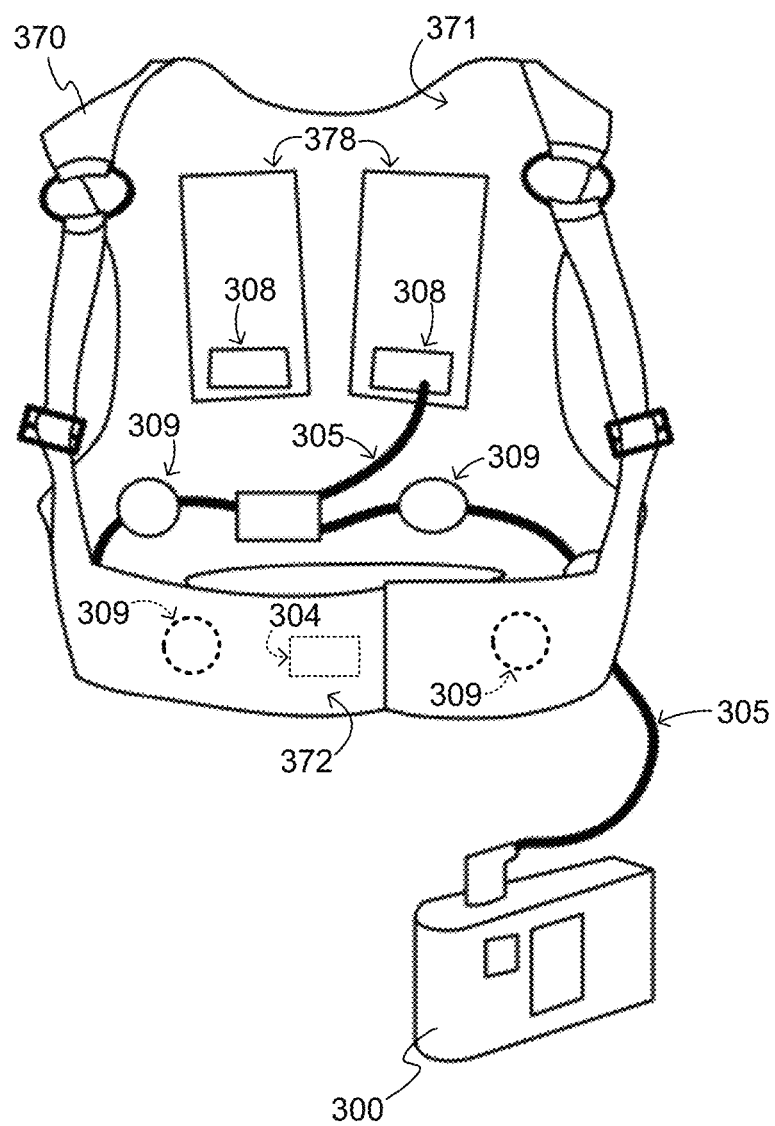
FIG. 4 is a diagram of sample embodiments of components of a multichannel WCD system, according to embodiments.

FIG. 4 is a diagram of sample embodiments of components of an WCD system with multichannel ECG monitoring. A support structure 370 includes a vest-like wearable garment. Support structure 370 has a back side 371, and a front side 372 that closes in front of the chest of the patient.

The WCD system of FIG. 4 also includes an external defibrillator 300, which in embodiments includes an AF detector (not shown) described below in conjunction with FIGS. 6-8. FIG. 4 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 5:
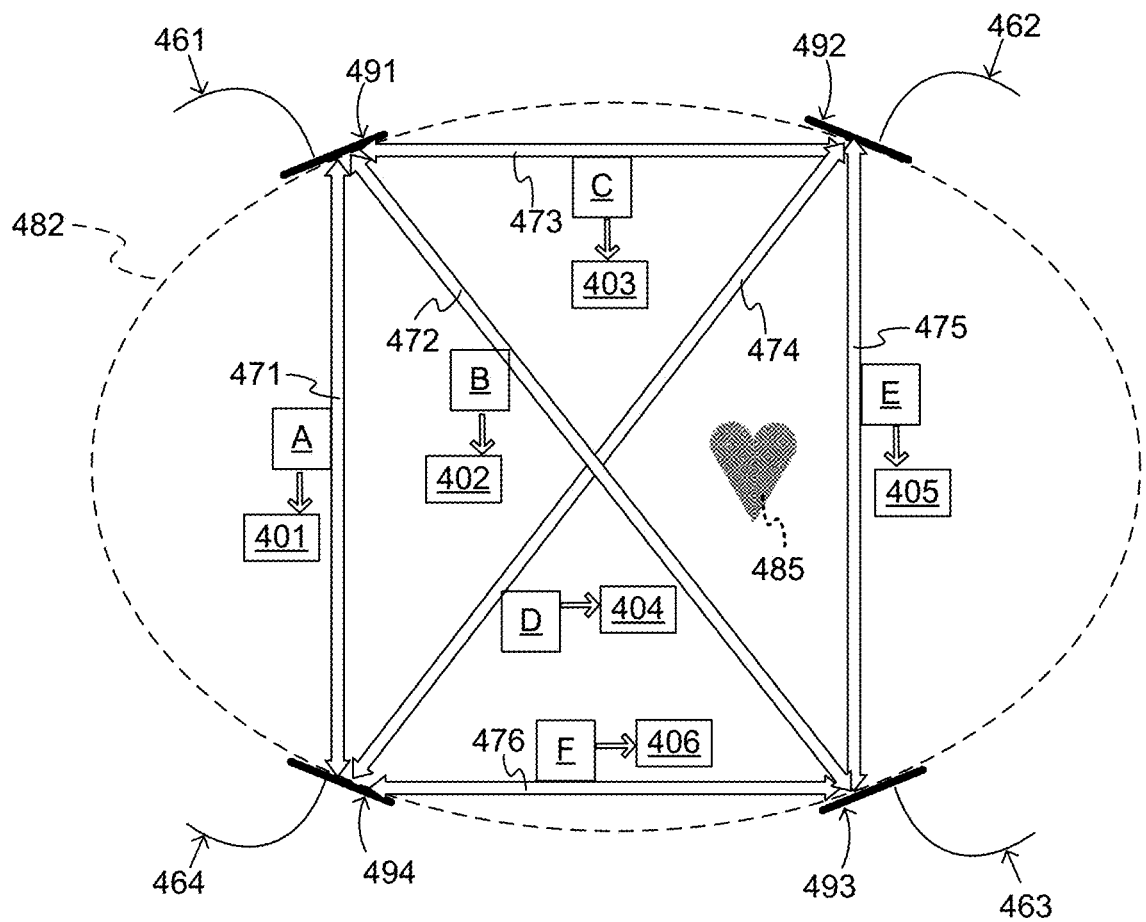
FIG. 5 is a conceptual diagram illustrating how multiple electrodes of a WCD system may be used for sensing ECG signals along different vectors, according to embodiments.

FIG. 5 is a conceptual diagram for illustrating how multiple electrodes of a WCD system may be used for sensing ECG signals along different vectors or channels, according to embodiments. As will be described below, these multiple vectors or channels can be used to detect AF and/or suspected AF and, optionally, determine AF Burden or other metric or metrics related to AF burden, as described below in conjunction with FIGS. 6-8. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either. Further, some embodiments average the voltages of all four electrodes electronically and then determine the voltage of each electrode relative to the average value. Conceptually this average value is the signal at some point in space in between the 4 electrodes. It continuously changes its virtual position based on the voltages of the 4 electrodes. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In embodiments, the vectors are formed in software by selecting a pair of these signals and subtracting one from the other. So for example, E1C−E2C=(E1−CM)−(E2−CM)=E1−E2+(CM−CM)=E1−E2=E12. Although six vectors are described in FIG. 4, in other embodiments a different number of vectors may be vectors may be used depending on the number of ECG electrodes used in the system and the desired number of vectors (up to the number of vectors than can be derived from the number of electrodes).

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017, entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Figure 6:
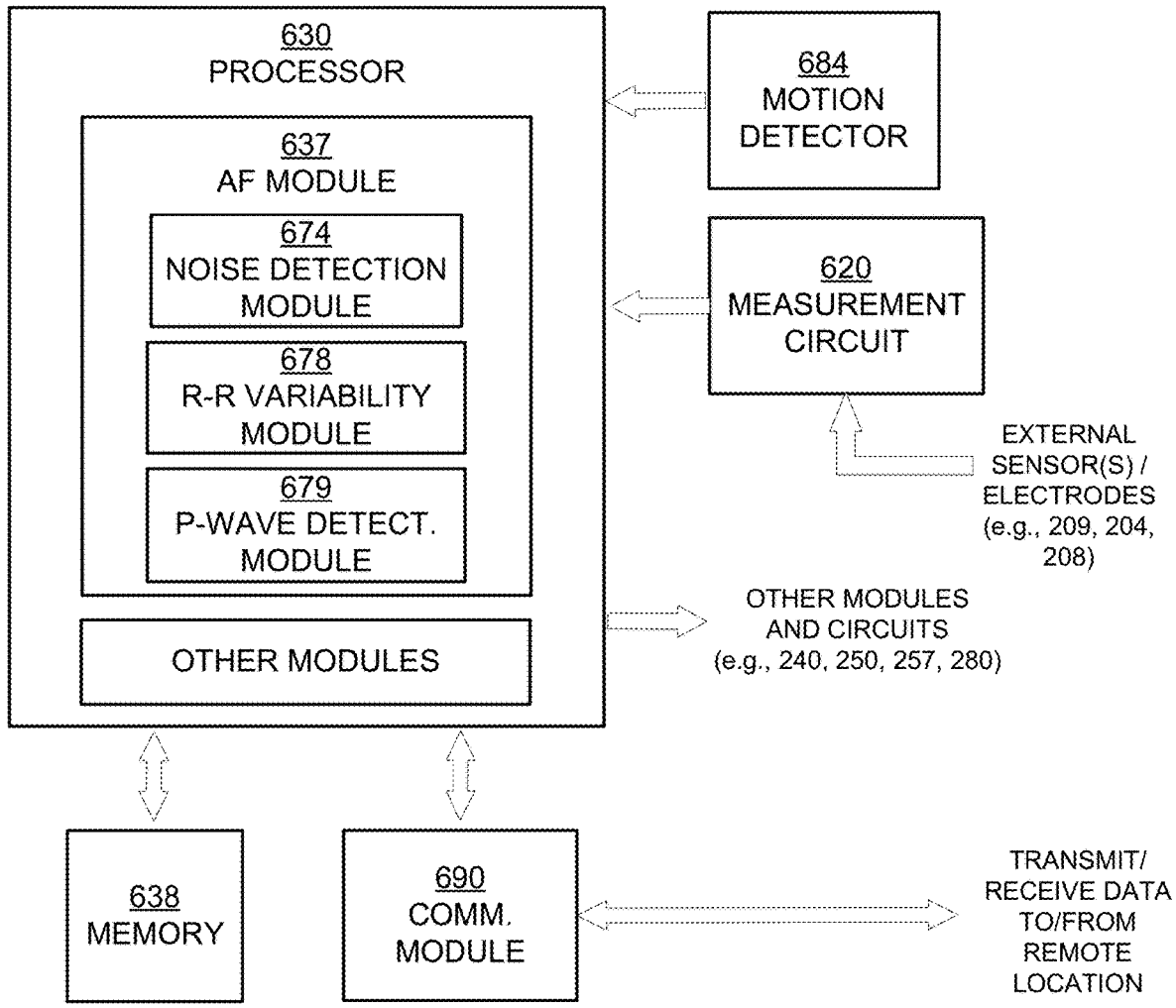
FIG. 6 is a diagram illustrating some components of a WCD system used in AF detection, according to embodiments.

FIG. 6 is a diagram illustrating some components of a WCD system used in AF detection, according to embodiments. In this example, the WCD system is similar to the WCD system of FIG. 2, and includes an external defibrillator 600 similar to external defibrillator 200 (FIG. 3).

In embodiments, external defibrillator 600 includes a measurement circuit 620, a processor 630, memory 638, motion detector 684, and a communication module 690, which are substantially similar to measurement circuit 220, processor 230, memory 238, motion detector 284, and communication module 290 described above. Other components of external defibrillator 600 (e.g., components corresponding to electrodes 204 and 208, defibrillation port 210, ECG electrodes 209, ECG port 219, power source 240, energy storage module 252, etc.) are omitted for clarity.

In embodiments, processor 630 includes an AF module 637 and other modules substantially similar to detection module 232, advice module 234, and other module 236, described above. AF module 637 includes a noise detection module 674, an R-R variability module 678, and a P-wave detection module 679, in some embodiments.

Noise detection module 674 is configured with one or more noise detection algorithms to detect noisy ECG signals. In some embodiments, the noise detection algorithms can include algorithms such as described in U.S. Pat. No. 10,918,879B2 entitled "WEARABLE CARDIOVERTER DEFIBRILLATOR (WCD) SYSTEM REACTING TO HIGH-AMPLITUDE ECG NOISE", U.S. Pat. No. 10,960,220B2 entitled "WEARABLE CARDIOVERTER DEFIBRILLATOR (WCD) SYSTEM EVALUATING ITS ECG SIGNALS FOR NOISE ACCORDING TO TALL PEAK COUNTS", and U.S. Patent Application Pub. No. US20190030351A1 entitled "WEARABLE CARDIOVERTER DEFIBRILLATOR (WCD) SYSTEM REACTING TO HIGH-FREQUENCY ECG NOISE", all of which are incorporated herein in their entireties for all purposes.

R-R variability module 678 is configured with one or more algorithms to analyze ECG signals to detect R-waves, measure the R-R interval of successive R-waves, and measure the variability of the measured R-R intervals. In some embodiments, R-R variability module 678 can include algorithms and processing for measuring R-R intervals and R-R variability as described in U.S. Pat. No. 10,105,547B2 entitled "WEARABLE CARDIOVERTER DEFIBRILLATOR (WCD) CAUSING PATIENT'S QRS WIDTH TO BE PLOTTED AGAINST THE HEART RATE" and U.S. Pat. No. 10,940,324B2 entitled "WEARABLE CARDIO- VERTER DEFIBRILLATOR (WCD) SYSTEM COMPUTING HEART RATE FROM NOISY ECG SIGNAL", all of which are incorporated herein in their entireties for all purposes. In some embodiments, when the measured R-R variability exceeds a preset threshold, R-R variability module 678 outputs a signal indicating that it has detected AF.

P-wave detection module 679 is configured with one or more algorithms to analyze ECG signals to detect P-waves. As will be described below, the presence of detected P-waves may be an indication that the patient does not have AF. As such, P-wave detection can be important for ruling out AF. In some embodiments, P-wave detection module 679 can include one or more algorithms that detect P-waves by detecting QRS complexes and detecting small peaks (i.e., the P-waves) at the expected PR interval (e.g., 0.12-0.22 seconds before the of the QRS complex). In some embodiments, P-wave detection module 679 can include algorithms for detecting P-waves as described in U.S. Patent Application Publication No. US20210205618A1 entitled "ASYSTOLE AND COMPLETE HEART BLOCK DETECTION" which is incorporated herein in its entirety for all purposes. In some embodiments, P-wave detection module 679 can include one or more algorithms for detecting P-waves as described in Hossain, Billal et al. "An Accurate QRS complex and P wave Detection in ECG Signals using Complete Ensemble Empirical Mode Decomposition Approach." IEEE access: practical innovations, open solutions vol. 7 (2019): 128869-128880. In some embodiments, P-PATENT waves may be detected with both a positive and a negative deflection. The polarity of the P-wave may be the same as the R-wave or it may be different. In some embodiments multiple candidate peaks may be detected and a P-wave discrimination algorithm applied to determine which peak is the true P-wave. Candidate peaks would be any deflection from baseline in the expected time interval (0.12-0.22 seconds before the start of the QRS complex) that is above the noise floor but less than about 0.25 mV peak amplitude. The true P-wave would be the one that matches previously-detected P-waves most closely in terms of location, amplitude, and morphology.

In some embodiments, the P-wave detection module may also detect atrial flutter waves. Atrial flutter waves can occur at very high rates (e.g. 250-350 per minute) and may be higher amplitude than normal P-waves. There are often multiple (e.g. 2-5) flutter wave peaks for every QRS complex. Flutter waves may occur at a regular rate, as is the case for an atrial flutter patient, or may occur at an irregular rate, as is the case for an atrial fibrillation (AF) patient. Atrial flutter waves are not always present in patients with AF, but if they are visible in the ECG they provide a positive indication of the presence of AF. In some embodiments, AF module 637 is configured to receive multiple channels of ECG signal and for each channel, run one or more R-R variability algorithms using R-R variability module 678. AF module 637 uses all of the channels' algorithm results to classify the ECG signal as AF or No AF. In some embodiments, the ECG signals received by processor 630 via measurement circuit 620 are divided into segments, each of which is analyzed using the R-R variability algorithm. In some embodiments, the segments are about 4.8 seconds in duration, but can range from 1 to 30 seconds in other embodiments. In some embodiments, the segments are overlapping segments with an overlap of 50%, but in other embodiments, the overlap can range from 0% to 90%. In some embodiments, AF module 637 classifies the ECG signal as AF or No AF based on the outcomes for each channel. For example, in some embodiments the number of channels with AF outcomes is compared to the number of channels with No AF outcomes, and AF module 637 classifies the ECG signal with the outcome having the higher number of channels. For example, in a three channels system, if two channels classify as AF and only one channel classifies as No AF, then AF module 637 classifies the ECG signal as AF. In embodiments in which more than one R-R variability algorithm is run on each channel, the number of channel classifications for AF is compared to the number of channel classifications for No AF to determine the classification output by AF module 637.

In some embodiments, AF module 637 is configured to receive multiple channels of ECG signal and for each channel, run one or more atrial wave detection algorithms using P-wave detection module 679. AF module 637 uses all of the channels' algorithm results to classify the ECG signal as AF or No AF. In some embodiments, AF module 637 can classify the ECG signal in a manner similar to a classification scheme described above for embodiments that use one or more R-R algorithms. In some embodiments, AF module 637 may be configured to receive multiple channels of ECG signals to analyze using P-wave detection module 679, but only those channels most likely to show atrial activity. For example, the V1 vector from a diagnostic 12 lead ECG is known to show atrial activity more prominently than other vectors. While a WCD may not record a V1 vector as a diagnostic 12 lead device does, there may be WCD vectors that are similar to V1. Those vectors may be most suitable for P-wave detection.

In some embodiments, AF module 637 is configured to receive multiple channels of ECG signal and for each channel run one or more R-R variability algorithms and one or more atrial wave detection algorithms. For example, in some embodiments, one R-R variability algorithm and one atrial wave algorithm are run on each channel using R-R variability module 678 and P-wave detection module 679. In other embodiments, one or more channels are analyzed using only an R-R variability algorithm while one or more other channels are analyzed using only an atrial wave algorithm. In some embodiments, the algorithm selected for each channel may be based on noise level associated with that channel. For example, an AF detection algorithm that is relatively less sensitive to noise may be selected for channels associated with relatively high noise levels, while an algorithm that is more sensitive to noise (but perhaps with higher specificity for AF detection) may be selected for channels associated with relatively low noise levels. The noise levels associations can be based on past data analyzed from previous patients and programmed into AF module 637. In other embodiments, the associations can be based on analysis of each channel from the current patient and used by processor 630 to select or modify the algorithm to use for each channel. For example, in some embodiments, noise detection module 674 is used to associate noise levels to channels. AF module 637 uses all of the channels' algorithm results to classify the ECG signal as AF or No AF. In some embodiments, AF module 637 can classify the ECG signal in a manner similar to a classification scheme described above for embodiments that use one or more R-R algorithms.

In some embodiments, AF module 637 is configured to receive multiple channels of ECG signal and for each channel, run one or more AF detection algorithms and a noise detection algorithm using noise detection module 674. In some embodiments, the AF detection algorithm is an R-R variability algorithm (e.g., using R-R variability module 678), while in other embodiments, the AF detection algorithm is an atrial wave detection algorithm (e.g., using P-wave detection module 679). In still other embodiments, one or more channels are analyzed using one AF algorithm while one or more other channels are analyzed using another AF algorithm. In still other embodiments, two different AF algorithms are used to analyze each channel. AF module 637 uses all of the channels' algorithm results including the results from noise detection module 674 to classify the ECG signal as AF or No AF. For example, in some embodiments, AF module 637 can classify the ECG signal in a manner as summarized in FIG. 7.

As shown in row 710 of FIG. 7, in some embodiments if all of the channel results classify as AF, then AF module 637 classifies the ECG signal as AF, no matter what the noise algorithm outputs. Similarly, if all of the channel results classify as No AF, then AF module 637 classifies the ECG signal as No AF, as shown in row 720. However, if all of the channel results classify as Noise, then AF module 637 classifies the ECG signal as Noise, as shown in row 730. If some of the channel results classify as AF and the remaining as Noise (i.e., no channels classify as No AF), then AF module 637 classifies the ECG signal as AF, as shown in row 740. In some embodiments, a preset minimum number of channels must classify as AF in order for AF module 637 to classify the ECG signal as AF. If some of the channel results classify as No AF and the remaining as Noise (i.e., no channels classify as AF), then AF module 637 classifies the ECG signal as No AF, as shown in row 750. In some embodiments, a preset minimum number of channels must classify as No AF in order for AF module 637 to classify the ECG signal as No AF. If one or more channels classify as AF, and one or more other channels classify as No AF and one or more still other channels classify as Noise, then AF module 637 classifies the ECG signal according to the higher of the number of AF channels vs No AF channels as shown in row 760. In some embodiments, if the number of AF channels is equal to the number of No AF channels, then AF module 637 classifies the ECG signal as No AF.

In some embodiments in which each channel is analyzed using multiple AF algorithms, then the result of each AF algorithm analysis is used instead of channel classification. That is, the first column of the table of FIG. 7 is modified so that "channels" is replaced with "AF algorithm classifications".

Some of the above embodiments can overcome challenges in using conventional AF detection approaches. Conventional approaches typically use one of two types of ECG measurements for detection of atrial fibrillation (AF): R-R interval variability, and atrial waves. See for example, the research paper "Comparative study of algorithms for Atrial Fibrillation detection" by Larburu et al (2011). This paper examines the methods used by 9 AF detection algorithms and states, "These methods are mainly based on two different characteristics of AF ECGs: the irregularity of RR intervals (RRI) and the fibrillatory electrical Atrial Activity (AA). The electrical AA is characterized by the absence of the P-wave (PWA) and special frequency properties (FSA)." Wearable devices that utilize dry ECG electrodes (e.g., currently available WCDs) may face challenges when attempting to detect AF because dry electrodes are more subject to noise than adhesive electrodes. In particular, conventional approaches for detecting atrial activity using dry electrodes may be unsatisfactory because of the relatively low level of the signal. Detecting atrial activity can be a challenge when using because P-waves are small, for example about 0.1 mV, which is about 10% of the amplitude of a QRS complex. A wearable device with dry electrodes (e.g., currently available WCDs) may be able to detect R-R variability, but that also can be confused by noise. The above described embodiments may be able to overcome these challenges by using multiple AF detection algorithms. For example, by using an algorithm that is less sensitive to noise when relatively high levels of noise are present and an algorithm with more specificity when the noise levels are relatively lower.

In some embodiments, a WMD system such as disclosed in FIGS. 1 and 2 is configured to provide an AF burden report and/or a report that characterizes AF burden, for example by including data when its AF algorithms classified the ECG signal as Noise. AF burden is typically defined as the percentage of time that the patient spends in AF. In some embodiments, the ECG signals analyzed by the WMD may be too noisy to allow AF burden to be assessed 100% of the time. In some embodiments, the WMD can classify the ECG signal as AF/No AF/Noise (as described above in conjunction with FIG. 7) and the AF burden assessment may be limited to periods when the ECG signal is relatively clean. In such embodiments, AF burden would be assessed only during periods not classified as noise. In some embodiments, the WMD device is configured to determine the AF burden and/or characterize the AF burden.

As previously described, reliably detecting atrial waves is typically much more difficult than detecting QRS complexes. In some embodiments, AF algorithms utilize atrial wave detection to classify the ECG signal as AF DETECTED or No AF, while in other embodiments an R-R variability algorithm alone is used to classify the ECG signal as AF SUSPECTED. Some embodiments use multiple algorithms for assessing AF burden on noisy signals. For example, the following two types of algorithms are used in some embodiments: a very specific algorithm (e.g., an atrial wave detection algorithm) that detects atrial activity, but can only be utilized when the signals are very clean, and a more noise tolerant algorithm (e.g., an R-R variability algorithm) but is less specific.

In embodiments, the specific algorithm would classify the ECG signal as AF DETECTED or No AF, and the noise-tolerant algorithm would classify the ECG signal as AF SUSPECTED or No AF. In embodiments, the WMD system includes an R-R variability module similar to R-R variability module 678 (FIG. 6) for the noise tolerant algorithm, and a P-wave detection module similar to P-wave detection module 679 (FIG. 6) for the specific algorithm. The WMD system would decide which algorithm to use based on a noise assessment of the signal. For example, in some embodiments, a WMD system may include a noise detection module similar to noise detection module 674 (FIG. 6) for the noise assessment to detect noise, which the WMD system uses to select between the specific algorithm and noise tolerant algorithm.

In some embodiments, the WMD system can provide a report that characterizes the AF burden. In some embodiments, the report includes the percentages of time that the patient's ECG signals were classified as NO AF, AF DETECTED, AF SUSPECTED, and Noise. FIG. 8 illustrates an example table 800 of the percentages that can be included in the report. In this example, the percentage of time the ECG signals were classified as NO AF is in a row 820 of table 800. This percentage can include the classifications by both the specific algorithm and the noise-tolerant algorithm. The percentage of time the specific algorithm classified the ECG signals as AF DETECTED is in a row 830. The percentage of time the noise-tolerant algorithm classified the ECG signals as AF SUSPECTED is in a row 840. The percentage of time the noise detection module classified the ECG signals as Noise is in a row 850.

In some embodiments, the WMD of the WMD system can perform these algorithms on ECG signals collected over a period of time (e.g., hourly, every 2 hours, daily, etc.) to generate reports characterizing the patient's AF burden. In some embodiments, the WMD can communicate the ECG signals collected over a period of time as described above to a remote location of the WMD system (e.g., a smart device such as a smartphone or tablet or notebook computer, or a server or cloud-based service) at which these algorithms on ECG signals and generate a report characterizing the AF burden as described above. In some embodiments, the percentages add up to 100%. In other embodiments, the classifications of both specific and noise-tolerant algorithms are used on all of the ECG signals (rather than being selected based on the noise assessment). For example, the AF DETECTED row may contain the percentage of time corresponding to the time periods in which both AF DETECTED and AF SUSPECTED occurred, while the AF SUSPECTED row may contain the percentage of time corresponding to the time periods in which the specific algorithm classified No AF and the noise-tolerant algorithm classified as AF SUSPECTED. Still further, in some embodiments, the report may include AF burden in addition to the AF burden characterization. For example, the AF burden can be calculated using AF DETECTED time divided by the AF DETECTED+NO AF time.

In some embodiments, the WMD system is configured so that the algorithms and settings for the algorithms can be selected. For example, the patient's physician may select that the WMD system use only one of the AF detection algorithms.

In some embodiments, the specific algorithm could be run on some channels and the noise-tolerant algorithm could be run on other channels, based on the noise assessment of each channel. Results could be reconciled if different channels disagreed using voting schemes similar to that described above for row 760 (FIG. 7).

In some embodiments, these algorithms could be run in real-time on the WCD, while in other embodiments they could be run after the fact on the WCD, or on a smartphone or tablet, or after being communicated to a server via network connection or memory device transfer, for example.

The devices and/or systems mentioned in this document perform functions, processes and/or methods. These functions, processes and/or methods may be implemented by one or more devices that include logic circuitry. Such a device can be alternately called a computer, a processor and so on. It may be a standalone device or computer, such as a general-purpose computer, special purpose computer, or part of a device that has one or more additional functions. The logic circuitry may include a processor and non-transitory computer-readable storage media, such as memories, of the type described above in this document. Often, for the sake of convenience, it is preferred to implement and describe a program as various interconnected distinct software modules or features. These, along with data are individually and also collectively known as software. In some instances, software is combined with hardware, in a mix called firmware.

This detailed description includes flow charts, algorithms, and symbolic representations of program operations, which according to some embodiments may be implemented within at least one computer readable medium. Embodiments of flow charts described herein may implement methods, programs, software, firmware, etc.

Figure 9:
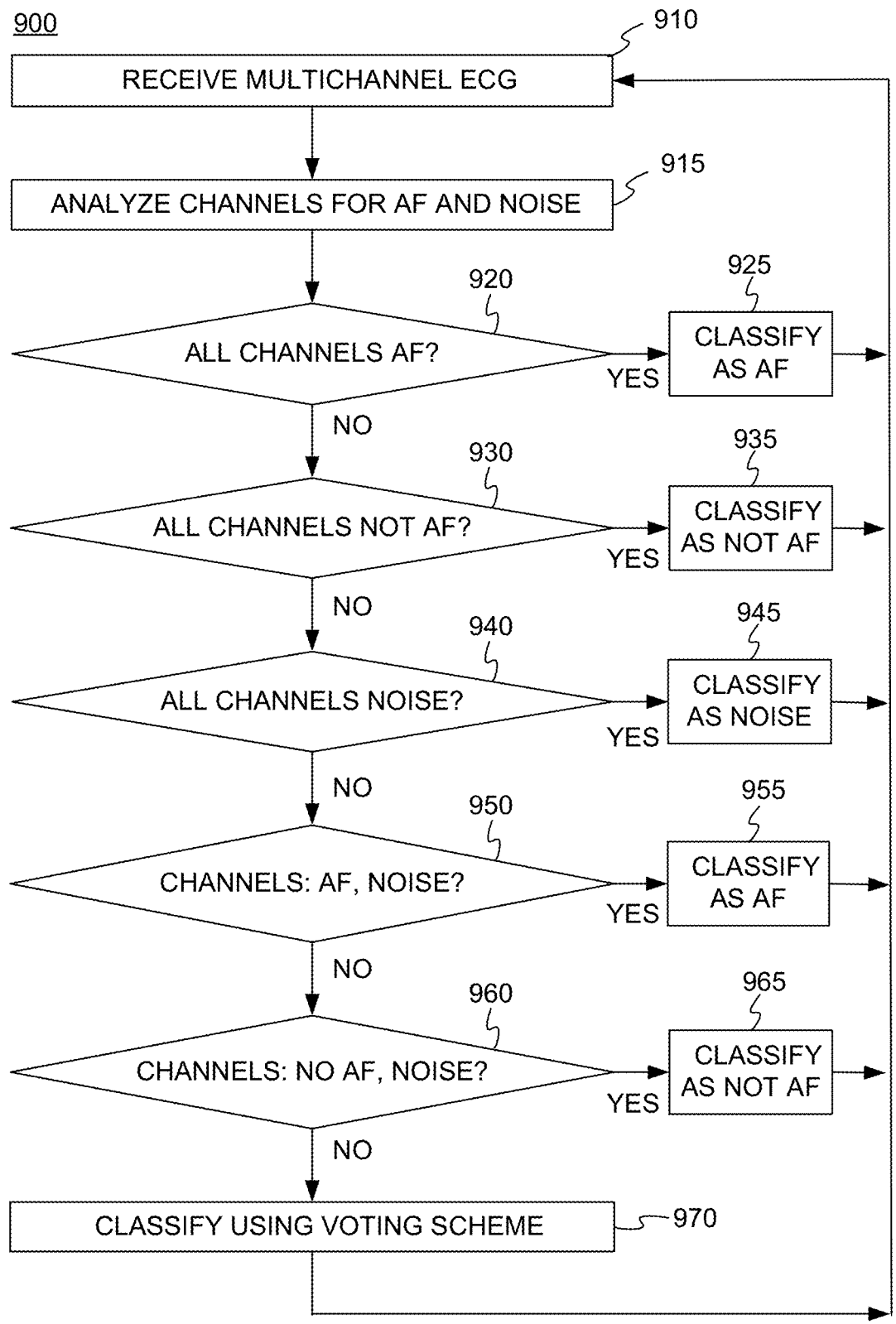
FIG. 9 is a flow diagram illustrating sample methods for use in a wearable medical device system to detect AF, according to embodiments.

FIG. 9 is a flow diagram illustrating a method 900 for use in a WMD system to detect AF (such as described above in conjunction with FIGS. 1-8) to detect AF. Method 900, in some embodiments, can start when the WMD system begins monitoring the patient's ECG.

In an operation 910 the WMD system receives multichannel ECG signals sensed from the patient using the WMD system. In some embodiments, a processor such as processor 630 (FIG. 6) receives the multichannel ECG signals via ECG electrodes and a measurement circuit such as ECG electrodes and measurement circuit 620 (FIG. 6). In some embodiments, a remote server or cloud-based service receives measurements of multichannel ECG from a WMD, for example by wired communication, wireless communication, memory device transfer, or a combination thereof.

In an operation 915, the received multichannel ECG signals are analyzed for AF and noise. In embodiments, this analysis includes running AF detection and noise detection algorithms to classify each channel of the received ECG is as AF, No AF (or Not AF), and Noise. In some embodiments, a processor such as processor 630 configured with AF module 637 (FIG. 6) analyzes the received multichannel ECG signals. In some embodiments, a remote server or cloud-based service performs the analysis.

In an operation 920, all of the classifications of all of the channels are analyzed to determine if they are all AF. If all of channels are classified as AF, method 900 proceeds to an operation 925 in which the ECG signal is classified as AF and returns to operation 910. In some embodiments, a processor such as processor 630 configured with AF module 637 (FIG. 6) classifies the ECG signal. In some embodiments the WMD system includes a smart device (e.g., a smartphone or tablet) and/or a remote server or cloud-based service that analyzes the channel classifications and classifies the ECG signal.

If in operation 920 not all of the channels are classified as AF, method 900 proceeds to an operation 930 in which all of the classifications of all of the channels are analyzed to determine if they are all NOT AF. If all of channels are classified as NOT AF, method 900 proceeds to an operation 935 in which the ECG signal is classified as NOT AF and returns to operation 910. In some embodiments, a processor such as processor 630 configured with AF module 637 (FIG. 6) analyzes the channel classifications and classifies the ECG signal. In some embodiments, the WMD system includes a smart device (e.g., a smartphone or tablet) and/or a remote server or cloud-based service that analyzes the channel classifications and classifies the ECG signal.

If in operation 930 not all of the channels are classified as NOT AF, the method proceeds to an operation 940 in which all of the classifications of all of the channels are analyzed to determine if they are all Noise. If all of channels are classified as Noise, method 900 proceeds to an operation 945 in which the ECG signal is classified as Noise and returns to operation 910. In some embodiments, a processor such as processor 630 configured with AF module 637 (FIG. 6) analyzes the channel classifications and classifies the ECG signal. In some embodiments, the channel classifications and classifies the ECG signal.

If in operation 940 not all of the channels are classified as Noise, the method proceeds to an operation 950 in which all of the classifications of all of the channels are analyzed to determine if they are all either AF or Noise (i.e., there are no NOT AF channel classifications). If all of channels are classified as either AF or Noise, method 900 proceeds to an operation 955 in which the ECG signal is classified as AF and returns to operation 910. In some embodiments, a processor such as processor 630 configured with AF module 637 (FIG. 6) analyzes the channel classifications and classifies the ECG signal. In some embodiments, the WMD system includes a smart device (e.g., a smartphone or tablet) and/or a remote server or cloud-based service that analyzes the channel classifications and classifies the ECG signal.

If in operation 950 not all of the channels are classified as either AF or Noise, the method proceeds to an operation 960 in which all of the classifications of all of the channels are analyzed to determine if they are all either NOT AF or Noise (i.e., there are no AF channel classifications). If all of channels are classified as either NOT AF or Noise, method 900 proceeds to an operation 965 in which the ECG signal is classified as NOT AF and returns to operation 910. In some embodiments, a processor such as processor 630 configured with AF module 637 (FIG. 6) analyzes the channel classifications and classifies the ECG signal. In some embodiments, the WMD system includes a smart device (e.g., a smartphone or tablet) and/or a remote server or cloud-based service that analyzes the channel classifications and classifies the ECG signal.

If in operation 960 not all of the channels are classified as either NOT AF or Noise, method 900 proceeds to an operation 970 in which a voting scheme or other reconciliation algorithm is applied to the channel classifications. In some embodiments, the ECG signal is classified according to the channel classification having the highest number of channels (i.e., can include classification as Noise in some embodiments). In other embodiments, the reconciliation algorithm classifies the ECG signal as AF if the number of AF channel classifications is greater than or equal to the number of NOT AF classifications (i.e., disregarding the number of Noise channel classifications), and as NOT AF if the number of AF channel classifications is less than the number of NOT AF classifications. Method 900 then returns to operation 910. In some embodiments, a processor such as processor 630 configured with AF module 637 (FIG. 6) analyzes the channel classifications and classifies the ECG signal. In some embodiments the WMD system includes a smart device (e.g., a smartphone or tablet) and/or a remote server or cloud-based service that analyzes the channel classifications and classifies the ECG signal.

Figure 10:
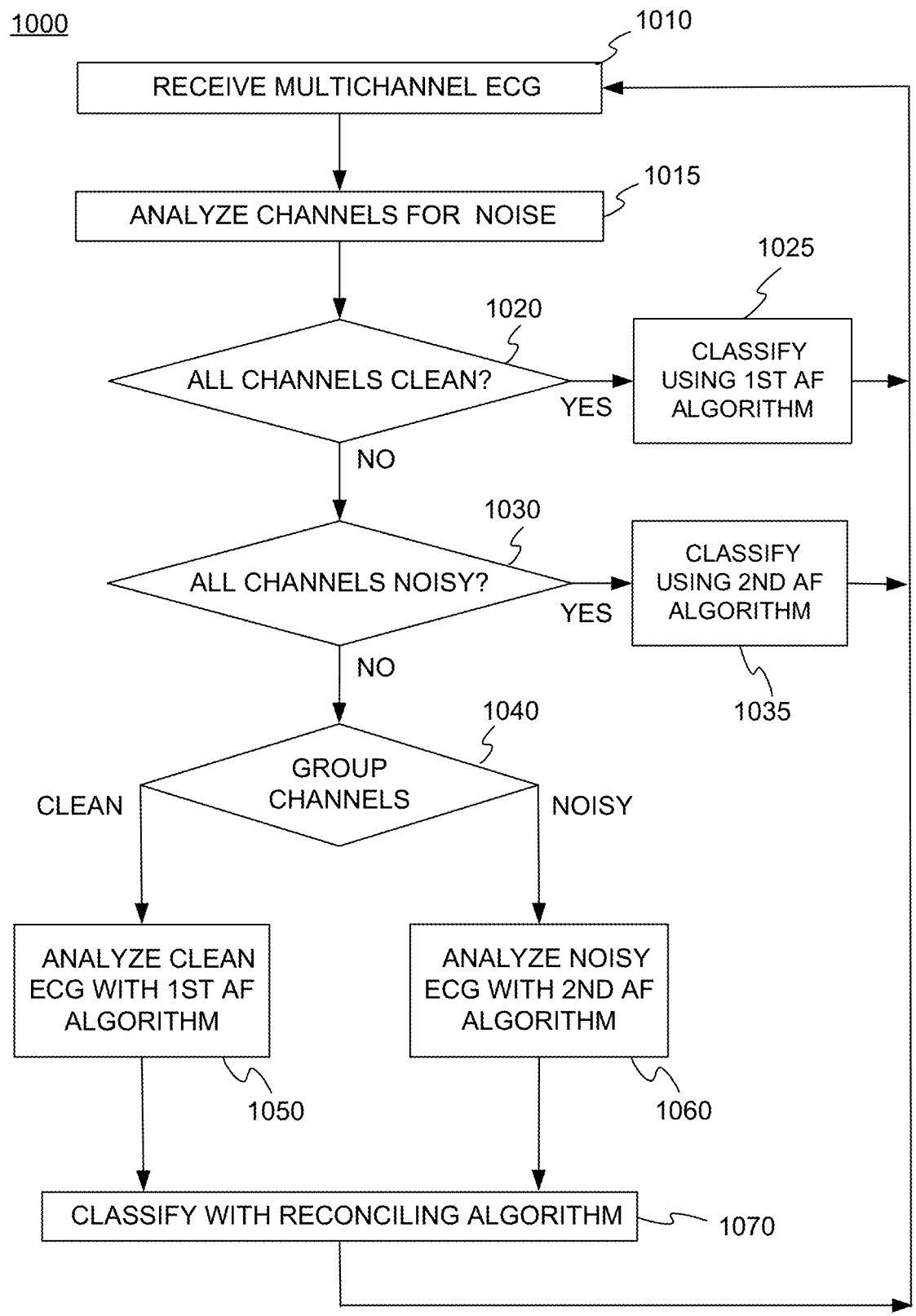
FIG. 10 is a flow diagram illustrating sample methods for use in a wearable medical device system to detect AF, according to other embodiments.

FIG. 10 is a flow diagram illustrating a method 1000 for use in a WMD system to detect AF (such as described above in conjunction with FIGS. 1-8) to detect AF. Method 1000, in some embodiments, can start when the WMD system begins monitoring the patient's ECG.

In an operation 1010 the WMD system receives multichannel ECG signals sensed from the patient using the WMD system. In some embodiments, a processor such as processor 630 (FIG. 6) receives the multichannel ECG signals via ECG electrodes and a measurement circuit such as ECG electrodes and measurement circuit 620 (FIG. 6). In some embodiments, a remote server or cloud-based service receives measurements of multichannel ECG from a WMD, for example by wired communication, wireless communication, memory device transfer, or a combination thereof.

In an operation 1015, the received multichannel ECG signals are analyzed for noise. In embodiments, this analysis includes running one or more noise detection algorithms to classify each channel of the received ECG is as either Noisy or Clean. For example, a received channel ECG can be classified as Noisy if the detected noise level exceeds a threshold or other criteria. In some embodiments, a processor such as processor 630 configured with AF module 637 (FIG. 6) analyzes the received multichannel ECG signals. In some embodiments, a remote server or cloud-based service performs the analysis.

In an operation 1020, all of the noise classifications of all of the channels are analyzed to determine if they are all classified as Clean. If all of channels are classified as Clean, method 1000 proceeds to an operation 1025 in which the multichannel ECG signal is classified as either AF or NOT AF using a first AF algorithm. In some embodiments, the first AF algorithm is a high specificity algorithm such as a P-wave detection algorithm. Method 1000 then returns to operation 1010. In some embodiments, a processor such as processor 630 configured with AF module 637 (FIG. 6) analyzes the channel ECG and classifies the ECG signal. In some embodiments the WMD system includes a smart device (e.g., a smartphone or tablet) and/or a remote server or cloud-based service that analyzes the channel ECG and classifies the ECG signal.

If in operation 1020 not all of the channels are classified as Clean, method 1000 proceeds to an operation 1030 in which all of the noise classifications of all of the channels are analyzed to determine if they are all Noisy. If all of channels are classified as Noisy, method 1000 proceeds to an operation 1035 in which the multichannel ECG signal is classified as either AF or NOT AF using a second AF algorithm. In some embodiments, the second AF algorithm is a noise-tolerant algorithm such as a R-R variability algorithm. Method 1000 then returns to operation 1010. In some embodiments, a processor such as processor 630 configured with AF module 637 (FIG. 6) analyzes the channel ECG and classifies the ECG signal. In some embodiments the WMD system includes a smart device (e.g., a smartphone or tablet) and/or a remote server or cloud-based service that analyzes the channel ECG and classifies the ECG signal.

If in operation 1030 not all of the channels are classified as Noisy, method 1000 proceeds to an operation 1040 in which the channels classified as Clean are grouped together and the channels classified Noisy are grouped together. In some embodiments, a processor such as processor 630 configured with AF module 637 (FIG. 6) groups the channels. In some embodiments, a remote server or cloud-based service groups the channels.

In an operation 1050, the channel ECG of the channels classified as Clean in operation 1030 are analyzed using the first AF algorithm, and in an operation 1060, the channel ECG of the channels classified as Noisy in operation 1030 are analyzed using the second AF algorithm. In some embodiments, a processor such as processor 630 configured with AF module 637 (FIG. 6) performs the analyses using the first and second AF algorithms. In some embodiments, a remote server or cloud-based service performs the analyses using the first and second AF algorithms.

In an operation 1070 the classification results from operations 1050 and 1060 are analyzed using a voting scheme or other reconciling algorithm to classify the ECG signal as AF or NOT AF. For example, if all of the channel classifications from operations 1050 and 1060 are all AF, then the ECG signal is classified as AF. Similarly if all of the channel classifications from operations 1050 and 1060 are all NOT AF, then the ECG signal is classified as NOT AF. If the channel classifications from operations 1050 and 1060 are a combination of AF and NOT AF, in some embodiments the ECG signal is classified as AF or NOT AF according to the channel classification having the highest number of channels. For example, the reconciliation algorithm can classify the ECG signal as AF if the number of AF channel classifications is greater than the number of NOT AF classifications, and NOT AF if the number of AF channel classifications is less than or equal to the number of NOT AF classifications. Method 1000 then returns to operation 1010. In some embodiments, a processor such as processor 630 configured with AF module 637 (FIG. 6) analyzes the channel classifications and classifies the ECG signal. In some embodiments the WMD system includes a smart device (e.g., a smartphone or tablet) and/or a remote server or cloud-based service that analyzes the channel classifications and classifies the ECG signal.

In the methods described above, each operation can be performed as an affirmative act or operation of doing, or causing to happen, what is written that can take place. Such doing or causing to happen can be by the whole system or device, or just one or more components of it. After careful review of this disclosure, those skilled in the art will recognize that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device, or method.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component, or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component, or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable medical device (WMD) system for detecting atrial fibrillation (AF) in a patient capable of being ambulatory while using the WMD system, the WMD system comprising:
   a plurality of electrocardiogram (ECG) electrodes configured to sense a multichannel ECG signal while the patient is using the WMD system;
   a support structure configured to position at least one of the plurality of ECG electrodes to contact a body of the patient while the support structure is worn by the patient;
   one or more processors, communicatively coupled to the plurality of ECG electrodes, configured with:
      a first AF detection module configured to analyze the multichannel ECG signal using a first algorithm and output first information, and
      a second AF detection module configured to analyze the multichannel ECG signal using a second algorithm with a different noise tolerance from the first algorithm and output second information,
      wherein, based at least in part on the first information and the second information, the one or more processors determine whether the multichannel ECG signal is indicative of AF; and
   a communication module, communicatively coupled to the one or more processors, configured to:
      responsive to a determination that the multichannel ECG signal is indicative of AF, provide a notification that the AF has been detected.

2. The WMD system of claim 1, wherein the one or more processors are further configured with a noise detection module configured to analyze the multichannel ECG signal and output third information, and wherein the one or more processors determine whether the multichannel ECG signal is indicative of AF, based at least in part on the first information, the second information, and the third information.

3. The WMD system of claim 2, wherein responsive to the third information provided by the noise detection module, the one or more processors determine whether the multichannel ECG signal is indicative of noise.

4. The WMD system of claim 3, wherein the one or more processors analyze a plurality of multichannel ECG signals over a predetermined time period and determine AF burden over the predetermined time period without using ECG signals of the plurality of multichannel ECG signals that are determined to be indicative of noise.

5. The WMD system of claim 3, wherein the one or more processors analyze a plurality of multichannel ECG signals over a predetermined time period and characterize AF burden over the predetermined time period by providing a metric corresponding to an amount of time during the predetermined time period in which one or more ECG signals of the plurality of multichannel ECG signals were determined to be indicative of noise.

6. The WMD system of claim 3, wherein the one or more processors analyze a plurality of multichannel ECG signals over a predetermined time period and characterize AF burden over the predetermined time period by providing a metric corresponding to a first amount of time during the predetermined time period in which one or more ECG signals of the plurality of multichannel ECG signals were determined to be indicative of detected AF, and a metric corresponding to a second amount of time during the predetermined time period in which one or more ECG signals of the plurality of multichannel ECG signals were determined to be indicative of suspected AF.

7. The WMD system of claim 6, wherein the first algorithm determines the detected AF and the second algorithm determines the suspected AF.

8. The WMD system of claim 2, wherein the third information provided by the noise detection module includes information indicating one or more channels of the multichannel ECG signal meeting a noise criterion, and one or more channels of the multichannel ECG signal not meeting the noise criteria, and wherein the one or more processors use the first AF detection module to analyze the one or more channels that meet the noise criterion and the second AF detection module to analyze the one or more channels that do not meet the noise criterion.

9. The WMD system of claim 1, wherein the one or more processors analyze a plurality of multichannel ECG signals over a predetermined time period and determine AF burden over the predetermined time period.

10. The WMD system of claim 1, wherein the first algorithm comprises a high specificity AF algorithm and the second algorithm comprises a noise-tolerant AF algorithm with less specificity than the first algorithm.

11. The WMD system of claim 1, wherein the WMD comprises an external defibrillator.

12. A wearable medical device (WMD) system for detecting atrial fibrillation (AF) in a patient capable of being ambulatory while using the WMD system, the WMD system comprising:
   a plurality of electrocardiogram (ECG) electrodes configured to sense a multichannel ECG signal while the patient is using the WMD system;
   a support structure configured to position at least one of the plurality of ECG electrodes to contact a body of the patient while the support structure is worn by the patient;
   an AF detector, communicatively coupled to at least the plurality of ECG electrodes, configured to:
      analyze, using a first algorithm, the multichannel ECG signal, wherein the first algorithm outputs first information,
      analyze, using a second algorithm, the multichannel ECG signal, wherein the second algorithm has a different noise tolerance from the first algorithm and outputs second information,
      determine whether the multichannel ECG signal is indicative of AF based at least in part on the first information and the second information, and
      determine whether the multichannel ECG signal is indicative of suspected AF based at least in part on the first information and the second information; and
   a communication module, communicatively coupled to at least the AF detector, configured to:
      responsive to a determination that the multichannel ECG signal is indicative of AF, provide a notification that the AF has been detected, and
      responsive to a determination that the multichannel ECG signal is indicative of suspected AF, provide a notification that the suspected AF has been detected.

13. The WMD system of claim 12, wherein the AF detector is configured to analyze the multichannel ECG signal further using a noise detection algorithm, wherein the noise detection algorithm outputs noise analysis information, and wherein the AF detector is configured to determine whether the multichannel ECG signal is indicative of AF further based on the noise analysis information.

14. The WMD system of claim 13, wherein the noise analysis information includes information indicating one or more channels of the multichannel ECG signal that exceeded a noise criterion and one or more channels of the multichannel ECG signal that did not exceed the noise criterion.

15. The WMD system of claim 14, wherein the one or more channels that exceeded the noise criterion are analyzed using the first algorithm, and the one or more channels that did not exceed the noise criterion are analyzed using the second algorithm.

16. The WMD system of claim 14, wherein the AF detector is further configured to determine an AF burden over a predetermined time period without using the one or more channels of the multichannel ECG signal that exceeded the noise criterion.

17. The WMD system of claim 14, wherein the AF detector is further configured to:

determine a metric corresponding to a first amount of time over a predetermined time period in which the multichannel ECG signal was determined to be indicative of the detected AF, and determine another metric corresponding to a second amount of time over the predetermined time period in which the multichannel ECG signal was determined to be indicative of the suspected AF.

18. The WMD system of claim 12, wherein in response to a determination that the multichannel ECG signal is indicative of AF, the AF detector is further configured to determine an AF burden over a predetermined time period.

19. The WMD system of claim 12, wherein the first algorithm is used to determine the detected AF and the second algorithm is used to determine the suspected AF.

20. The WMD system of claim 12, wherein the first algorithm comprises a high specificity AF algorithm and the second algorithm comprises a noise-tolerant AF algorithm with less specificity than the first algorithm.

* * * * *